United States Patent
Ishikawa

(10) Patent No.: US 11,879,122 B2
(45) Date of Patent: Jan. 23, 2024

(54) TEMPERATURE-SENSITIVE *BACILLUS SUBTILIS NATTO* AND *NATTO* HAVING LOW SPORE CONTENT

(71) Applicant: MIZKAN HOLDINGS CO., LTD., Aichi (JP)

(72) Inventor: Atsushi Ishikawa, Aichi (JP)

(73) Assignee: Mizkan Holdings Co., Ltd., Aichi (JP)

( * ) Notice: Subject to any disclaimer, the term of this patent is extended or adjusted under 35 U.S.C. 154(b) by 1152 days.

(21) Appl. No.: 16/553,598

(22) Filed: Aug. 28, 2019

(65) Prior Publication Data

US 2019/0390288 A1 Dec. 26, 2019

Related U.S. Application Data

(63) Continuation of application No. PCT/JP2018/006872, filed on Feb. 26, 2018.

(30) Foreign Application Priority Data

Feb. 28, 2017 (JP) ................................ 2017-036652

(51) Int. Cl.
*C12N 1/20* (2006.01)
*A23L 11/50* (2021.01)
*C12R 1/125* (2006.01)

(52) U.S. Cl.
CPC ............... *C12N 1/20* (2013.01); *A23L 11/50* (2021.01); *C12N 1/205* (2021.05); *C12R 2001/125* (2021.05); *G01N 2333/956* (2013.01)

(58) Field of Classification Search
CPC .... C12N 1/20; C12N 1/205; C12R 2001/125; A23L 11/50
See application file for complete search history.

(56) References Cited

FOREIGN PATENT DOCUMENTS

| JP | 2006-6117 A | 1/2006 | | |
|----|----|----|----|----|
| JP | 2006-141209 A | 6/2006 | | |
| JP | 2011-10634 A | 1/2011 | | |
| JP | 2013-252069 A | 12/2013 | | |
| WO | WO-2015146730 A1 * | 10/2015 | .............. | A23L 11/09 |

OTHER PUBLICATIONS

P. Kerjan et al., "Characterization of a Thermosensitive Sporulation Mutant of Bacillus subtilis Affected in the Structural Gene of an Intracellular Protease", European Journal of Biochemistry, Aug. 1979, vol. 98, pp. 353-362 (10 pages).
H. Yoshikawa et al., "Temperature-Sensitive Sporulation Caused by a Mutation in the Bacillus subtilis secY Gene", Journal of Bacteriology, 1993, vol. 175, No. 11, pp. 3656-3660 (5 pages).
N. Mitsui et al., "Development of natto with germination-defective mutants of Bacillus subtilis (natto)", Applied Microbiology and Biotechnology, Mar. 2009, vol. 82, pp. 741-748 (8 pages).
International Search Report issued in International Application No. PCT/JP2018/006872, dated May 22, 2018 (2 pages).
Written Opinion issued in International Application No. PCT/JP2018/006872, dated May 22, 2018 (5 pages).

* cited by examiner

*Primary Examiner* — Ruth A Davis
(74) *Attorney, Agent, or Firm* — Osha Bergman Watanabe & Burton LLP

(57) ABSTRACT

A method of producing *natto* includes inoculating a mutant strain of *Bacillus subtilis* var. *natto* onto steamed or boiled soybeans, and fermenting the soybeans inoculated with the mutant strain by maintaining a temperature of the soybeans at 40° C. to 53° C. The number of the mutant strain spores after fermenting the soybeans is $5 \times 10^5$ or less spores per gram of the fermented soybeans. A single colony of the mutant strain cultured in a selective solid medium supplemented with biotin at a gas phase temperature of 49° C. for 48 hours has a region having a hue of yellow (Y), a value of 9 or more, and a chroma of 2 or less, as defined by the Munsell Color System, and a surface area of the region is 20% or less of the total surface area of the single colony.

13 Claims, 3 Drawing Sheets

TEMPERATURE-SENSITIVE *BACILLUS SUBTILIS NATTO* AND *NATTO* HAVING LOW SPORE CONTENT

REFERENCE TO A DEPOSIT OF BIOLOGICAL MATERIAL

This application contains a reference to one or more deposits of biological material, which deposit(s) are incorporated herein by reference.

TECHNICAL FIELD

One or more embodiments of the present invention relate to a temperature-sensitive *B. subtilis natto* mutant strain, which has a normal spore-forming ability in a temperature zone that is generally used in a liquid culture for obtaining a *Bacillus subtilis natto* starter for inoculation, but has a reduced spore-forming ability in a temperature zone that is generally used in *natto* fermentation, and *natto* having a small number of spores produced using the aforementioned mutant strain. More specifically, one or more embodiments of the present invention relate to: a *B. subtilis natto* mutant strain, which has a normal spore-forming ability upon a liquid culture for obtaining a *Bacillus subtilis natto* starter, but has a reduced spore-forming ability upon a fermentation step in the production of *natto*, because its spore-forming ability changes in a temperature-dependent manner; *natto* produced using the mutant strain, wherein the *natto* has a small number of spores and can be subjected to heat sterilization; a production method thereof; and a method for reducing the spores and vegetative cells of *Bacillus subtilis natto* in the *natto* produced using the mutant strain.

BACKGROUND

*Itohiki natto* (hereinafter simply referred to as "*natto*") prepared by fermenting soybeans with *Bacillus subtilis natto* is a traditional Japanese fermented food product. *Natto* containing an abundant amount of soybean protein has a high nutritive value, and has unique flavor and viscous texture. In recent years, it has been reported that *natto* has probiotic action, antibacterial action, and various types of health promotion actions provided by functional ingredients and the like (e.g., antithrombotic action, hypotensive action, hypocholesterolemic action, bone formation promoting action, fat burning action, etc.). Hence, *natto* is a food product which is increasingly demanded in recent years.

*Natto* is generally produced by subjecting raw material soybeans to a selection step, a washing step, a water immersion step, a steaming step, a *Bacillus subtilis natto* inoculation step, a filling step of filling soybeans into a container, a fermentation step, a cooling and aging step, and a wrapping step. In the fermentation step, as a result of the fermentation action by *Bacillus subtilis natto*, a threading ingredient containing polyglutamic acid as a main ingredient and having strong viscosity is generated. This threading ingredient has properties for imparting unique flavor and texture to *natto*. Moreover, as another result of the fermentation action by *Bacillus subtilis natto*, a *natto*-specific flavor ingredient mainly containing diacetyl, acetoin, pyrazines and the like, which is generally called "*natto* smell," is generated. A moderate concentration of such *natto* smell contributes, as a flavor unique to *natto*, to the improvement of the palatability of *natto*. On the other hand, as a result of *natto* fermentation, ammonia is also generated. Generation of excessive amount of ammonia causes unpleasant odor, leading to a reduction in the palatability.

Spore-forming bacteria that form bacterial spores (spores) such as the spores of *Bacillus subtilis natto* have two types of conditions, namely, vegetative cells and spores, depending on the environment. When the environment is not suitable for proliferation, the spore-forming bacteria form spores having high endurance and maintain a dormant state. In contrast, when the environment is suitable for proliferation, the spore-forming bacteria are germinated and become vegetative cells, which then repeat cell division. In the above-described step of producing *natto*, inoculation of *Bacillus subtilis natto* is carried out on high-temperature soybeans after completion of the steaming step. Accordingly, if *Bacillus subtilis natto* in the state of vegetative cells having low heat resistance were sprayed, the *Bacillus subtilis natto* would die, and favorable fermentation would not be carried out. Therefore, for the inoculation of *Bacillus subtilis natto*, *Bacillus subtilis natto* in the state of physically and chemically stable spores is generally used.

However, since the spores of *Bacillus subtilis natto* have extremely high heat resistance, if heat sterilization is performed at 100° C. or lower, the spores of *Bacillus subtilis natto* remain in the product, although the properties of *natto* can be maintained. In the case of common processed food products, there is a guideline for prevention of degradation that the viable count per gram of processed food product should be set at $1 \times 10^5$ to $1 \times 10^6$ orders or less within expiration date or best-before date. When the number of spores of *Bacillus subtilis natto* in a *natto* product is larger than the aforementioned guideline of the viable count in common processed food products, in a case where the *natto* itself is processed in the production line of common processed food products or the *natto* is used as a part of raw materials for processed food products, the spores of *Bacillus subtilis natto* adhere to the production line of processed food products, and it is likely that the spores of *Bacillus subtilis natto* are thereby mixed into other processed food products not containing *natto* that have produced in the production line. As a result, the use of *natto* for processed food products may be restricted.

To date, in order to reduce the spores of *Bacillus subtilis natto* (hereinafter simply referred to as "spores" at times) contained in *natto*, various approaches have been taken. A representative approach is heat sterilization. For sterilization of spores contained in *natto*, heating at approximately 120° C. is generally necessary. However, under such heating conditions, bitter taste may come out, or stickiness may disappear, or ammonia odor may be generated. Thus, it is difficult to retain the quality of *natto*. There is also a method of reducing the number of spores in *natto* by using *Bacillus subtilis natto* that hardly forms spores, or by applying fermentation conditions wider which spores are not formed.

For example, a method of performing a sterilization treatment on dry *natto* prepared by producing *natto* using *Bacillus subtilis natto* having a low spore formation rate and then drying the produced *natto* (see Patent Literature 1) and a method of performing sterilization on *natto* at a timing in which the vegetative cell percentage in *Bacillus subtilis natto* is high and the spore percentage therein is low (see Patent Literature 2) have been reported. However, in the case of the method of using dry *natto*, since the *natto* is not raw, a difference in the texture comes out. On the other hand, in the case of the sterilization at the timing of a low spore formation rate, since vegetative cells having low heat resistance are mainly sterilized, a considerable number of spores of *Bacillus subtilis natto* remain, unless a germination treatment is carried out by a special method such as addition of L-alanine. As such, this method is insufficient for reducing the number of spores. Therefore, according to both of these methods, the quality of natto is hardly guaranteed, and sterilization is insufficient.

Furthermore, a method for producing natto, using a B. subtilis natto mutant strain comprising a deletion of a spore-forming gene such as a sigK gene, has been reported (see Patent Literature 3). However, since the above-described spore-forming gene is associated with regulation of the expression of many genes specific to spore-forming stages such as formation of a spore coat as an outermost layer of spore, a normal spore-forming ability cannot be recovered in such gene destruction genes. Accordingly, even if the aforementioned B. subtilis natto mutant strain is used to perform a culture, it is difficult to form the spores of Bacillus subtilis natto, and thus, the cultured Bacillus subtilis natto is in the state of vegetative cells.

Hence, as mentioned above, since inoculation of Bacillus subtilis natto is performed on high-temperature soybeans after completion of a steaming step in the general step of producing natto, if a B. subtilis natto mutant strain, in which a spore-forming gene is destroyed as described above and so, which is in the state of vegetative cells, is inoculated into soybeans under high-temperature conditions, the vegetative cells having low heat resistance die (are significantly reduced), and natto fermentation cannot be carried out. Accordingly, upon inoculation of Bacillus subtilis natto, a step of decreasing the temperature of the steamed soybeans to create low-temperature conditions needs to be added. In addition, since such low-temperature conditions are applied, microbial contamination easily occurs, thereby causing sanitation problems.

CITATION LIST

Patent Literature

Patent Literature 1: JP Patent Publication (Kokai) No. 2006-6117 A
Patent Literature 2: JP Patent Publication (Kokai) No. 2006-141209 A
Patent Literature 3: JP Patent Publication (Kokai) No. 2011-10634 A

SUMMARY

One or more embodiments of the present invention provide a temperature-sensitive Bacillus subtilis natto, which has a normal spore-forming ability in a temperature zone that is generally used in a liquid culture for obtaining a Bacillus subtilis natto starter for inoculation, but has a reduced spore-forming ability in a temperature zone that is generally used in natto fermentation. One or more embodiments of the present invention provide natto having a small content of spores of Bacillus subtilis natto by applying existing equipment and existing steps, using the aforementioned Bacillus subtilis natto, without causing problems such as poor fermentation or microbial contamination.

The present inventor has surprisingly found that, when a B. subtilis natto mutant strain is cultured on a specific selective solid medium at a specific gas phase temperature and then, a colony exhibiting a specific surface color is selected, a B. subtilis natto mutant strain whose spore-forming ability is reduced in a temperature zone generally used in natto fermentation is comprised therein at a high rate, and that when natto is produced using this B. subtilis natto mutant strain in a temperature zone for common fermentation, natto with a low spore number can be obtained.

On the other hand, the above-described B. subtilis natto mutant strain has a normal spore-forming ability in a temperature zone that is commonly used in a liquid culture for obtaining a Bacillus subtilis natto starter for inoculation. If such a B. subtilis natto mutant strain does not have a sufficient spore-forming ability in a liquid culture for obtaining a Bacillus subtilis natto starter for inoculation, the concentration of the spores of Bacillus subtilis natto is decreased, and thus, some measures need to be taken, such as extension of culture time or an increase in the amount of the liquid medium used for the Bacillus subtilis natto starter. These measures result in non-negligible cost increase in the production of natto. In the case of using the present B. subtilis natto mutant strain in the production of natto, however, the aforementioned problems do not occur.

Moreover, since the Bacillus subtilis natto starter obtained by the liquid culture of the present B. subtilis natto mutant strain contains spores in a high concentration, as in the case of an ordinary Bacillus subtilis natto starter, even if it is inoculated into soybeans steamed at a high temperature, the spores of Bacillus subtilis natto sufficiently remain. As a result, sufficiently fermented natto can be produced, and it is not necessary to add a step of cooling the soybeans after completion of the steaming step. Also, there are no problems regarding microbial contamination.

One or more embodiments of the present invention include the following:

[1] A Bacillus subtilis natto (Bacillus subtilis var. natto) mutant strain having the following properties (A) to (C):
(A) when the total area of the surface of a single colony of the Bacillus subtilis natto mutant strain that has been allowed to grow by being cultured in a selective solid medium supplemented with biotin at a gas phase temperature of 49° C. for 48 hours is set at 100%, with regard to the surface color of the single colony according to the Munsell Color System, the area of a region having the hue of yellow (Y), a value of 9 or more, and a chroma of 2 or less is 20% or less,
(B) when the Bacillus subtilis natto mutant strain is cultured in a liquid medium for spore formation at a liquid temperature of 37° C., the number of spores of the B. subtilis natto mutant strain becomes $1 \times 10^7$ cells/ml or more, and
(C) when the B. subtilis natto mutant strain is inoculated into soybeans, such that the number of spores of Bacillus subtilis natto becomes $5 \times 10^3$ cells per gram of boiled soybeans or steamed soybeans, and the temperature of the soybeans is maintained in the range of 40° C. to 53° C., natto having favorable stickiness and favorable natto-specific flavor, in which the number of spores of Bacillus subtilis natto is $5 \times 10^5$ cells or less per gram of the natto can be produced.
[2] Natto, which is characterized in that it is produced using the B. subtilis natto mutant strain according to the above [1].
[3] The natto according to the above [2], wherein the number of spores of Bacillus subtilis natto is $5 \times 10^5$ cells or less per gram of the natto.
[4] The natto according to the above [2], which is characterized in that it is subjected to heat sterilization at 55° C. to 100° C. for 30 minutes to 2 hours after completion of fermentation.

[5] The *natto* according to the above [4], wherein the total number of cells of *Bacillus subtilis natto* is $1 \times 10^6$ cells or less per gram of the *natto*.

[6] A method for producing *natto*, comprising a step of fermenting soybeans using the *B. subtilis natto* mutant strain according to the above [1].

[7] The method for producing *natto* according to the above [6], wherein the number of spores of *Bacillus subtilis natto* after completion of the fermentation step is $5 \times 10^5$ cells or less per gram of the *natto*.

[8] The method for producing *natto* according to the above [7], further comprising a step of performing heat sterilization at 55° C. to 100° C. for 30 minutes to 2 hours after completion of the fermentation.

[9] The method for producing *natto* according to the above [8], wherein the total number of cells of *Bacillus subtilis natto* after completion of the heat sterilization is $1 \times 10^6$ cells or less per gram of the *natto*.

[10] A method for reducing the spores and vegetative cells of *Bacillus subtilis natto* in *natto*, which is characterized in that it comprises performing heat sterilization, after soybeans have been fermented using the *B. subtilis natto* mutant strain according to the above [1].

[11] The method for reducing the spores and vegetative cells of *Bacillus subtilis natto* in *natto* according to the above [10], wherein the heat sterilization is performed at 55° C. to 100° C. for 30 minutes to 2 hours after completion of the fermentation.

[12] A method for screening for *Bacillus subtilis natto* with a reduced spore-forming ability in a *natto* fermentation temperature zone, comprising the following steps (1) and (2):

(1) a step of culturing a test *Bacillus subtilis natto* in a selective solid medium supplemented with biotin at a gas phase temperature of 49° C. for 48 hours, and (2) a step of analyzing the surface color of a single colony of the test *Bacillus subtilis natto* formed on the selective solid medium as a result of the culture in the step (1), and then, selecting a test *Bacillus subtilis natto* that satisfies the following requirement: when the total area of the surface of the single colony is set at 100%, the area of a region having the hue of yellow (Y), a value of 9 or more and a chroma of 2 or less according to the Munsell Color System is 20% or less.

The present application claims priority from Japanese Patent Application No. 2017-036652, filed on Feb. 28, 2017; the disclosure of which is hereby incorporated by reference.

According to one or more embodiments of the present invention, *natto* having a small content of spores of *Bacillus subtilis natto* can be provided by applying existing equipment and existing steps, without causing problems such as poor fermentation or microbial contamination. In addition, since the *natto* according to one or more embodiments of the present invention has a small content of spores of *Bacillus subtilis natto*, heat sterilization can be carried out at a temperature at which the vegetative cells die (are significantly reduced). Therefore, the *natto* according to one or more embodiments of the present invention has a low risk of mixing the spores of *Bacillus subtilis natto* into a production line other than *natto*, etc., and thus, the present *natto* can be subjected to the production of various types of processed food products.

DETAILED DESCRIPTION OF EMBODIMENTS

Figure 1:
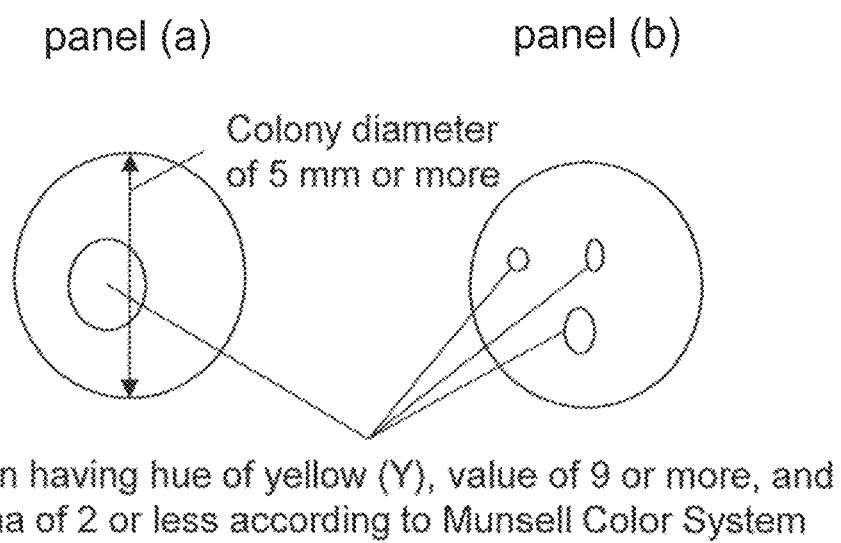
FIG. 1 is a schematic view showing one aspect of a method for screening for a *B. subtilis natto* mutant strain having a reduced spore-forming ability in a *natto* fermentation temperature zone, in which the surface color of a single colony is used as an indicator (panel (a): one roughly white region; panel (b) a plurality of roughly white regions).

Hereinafter, one or more embodiments of the present invention will be described in detail in the following specific embodiments.

1. *B. subtilis natto* Mutant Strain

The novel *B. subtilis natto* mutant strain according to one or more embodiments of the present invention (hereinafter referred to as "the *B. subtilis natto* mutant strain according to one or more embodiments of the present invention") is a temperature-sensitive *B. subtilis natto* mutant strain, which has a normal spore-forming ability in a temperature zone that is generally used in a liquid culture for obtaining a *Bacillus subtilis natto* starter for inoculation (seed fungus), but has a reduced spore-forming ability in a temperature zone that is generally used in *natto* fermentation. In one or more embodiments of the present invention, the "temperature zone that is generally used in a liquid culture for obtaining a *Bacillus subtilis natto* starter" is 28° C. to 37° C., and preferably 30° C. to 37° C. The "temperature zone that is generally used in *natto* fermentation" means a temperature zone, in which the temperature of soybeans can be substantially maintained at 40° C. to 53° C., and preferably at 43° C. to 50° C. In the case of an ordinary production method, room temperature is maintained in a temperature zone of 35° C. to 51° C., and preferably of 38° C. to 47° C., so that the temperature of soybeans during fermentation can be maintained in the above-described temperature zone. The temperature of soybeans differs from room temperature. This is because the temperature of soybeans is increased by heat of fermentation and thus, it is maintained in the above-described temperature zone.

[Microbiological Characteristics of *B. subtilis natto* Mutant Strain according to One or more Embodiments of the Present Invention]

As described below, the *B. subtilis natto* mutant strain according to one or more embodiments of the present invention has microbiological characteristics that are equivalent to those of the parent strain, regarding characteristics other than spore-forming ability. According, as with ordinary *Bacillus subtilis natto*, the *B. subtilis natto* mutant strain according to one or more embodiments of the present invention has properties capable of producing *natto* having good stickiness and fine appearance.

Herein, the *Bacillus subtilis natto* is a bacterium classified into a variant (*B. subtilis* var. *natto*, or *B. subtilis* (*natto*)) of *Bacillus subtilis*. Depending on the classification system, there may be a case where the *Bacillus subtilis natto* is classified as a related species of *Bacillus subtilis*, namely *Bacillus natto* (*B. natto*).

(a) Morphological Characteristics

The vegetative cell of the *B. subtilis natto* mutant strain according to one or more embodiments of the present invention is a bacterium having a size of approximately 2 to 3 μm and has motility. In addition, it has a gram staining property. The spore has an elliptical shape and a size of approximately 1.12 to 1.28 μm.

(b) Cultural Properties

The colony of the *B. subtilis natto* mutant strain according to one or more embodiments of the present invention on an LB agar medium (Table 3 of Example 1 described later) has a cyclic shape. The surface of the colony is characterized in that it has wrinkles, is lusterless, and has a color tone from opaque to milky white, with no apophysis in the center thereof. It is to be noted that the colony has viscosity on a medium rich in glutamic acid.

When the present *B. subtilis natto* mutant strain is cultured in a liquid medium, a fungal membrane is formed on the surface of the medium after completion of the culture. In addition, the culture solution becomes clouded.

The *B. subtilis natto* mutant strain according to one or more embodiments of the present invention satisfies the following requirement: when the *B. subtilis natto* mutant strain according to one or more embodiments of the present invention is cultured in a selective solid medium supplemented with biotin at a gas phase temperature of 49° C. for 48 hours, if the total area of the surface of a single colony of the *Bacillus subtilis natto* mutant strain is set at 100%, with regard to the surface color of the single colony according to the Mansell Color System, the area of a region having the hue of yellow (Y), a value of 9 or more, and a chroma of 2 or less is 20% or less. Herein, the "surface of a single colony" indicates a surface that can be confirmed by visual observation, when the colony that has grown on the selective solid medium supplemented with biotin is observed from the upper portion of a plate. Moreover, the above-described specific regions may be present in a plurality of sites, and in such a case, the area of a region means a total of the areas of the plurality of sites. The area of the above-described specific region is not limited, as long as it is 20% or less. The area of the specific region is preferably 15% or less, more preferably 10% or less, further preferably 5% or less, and most preferably 0%.

The "selective solid medium supplemented with biotin" is not particularly limited, as long as it is a solid medium commonly used in the culture of *Bacillus subtilis natto*, which comprises medium components such as a carbon source, a nitrogen source, and inorganic salts, enables the formation of the spores of *Bacillus subtilis natto* and the growth thereof, and enables observation of the colony thereof. For example, an agar medium for spore formation (containing B) (Table 4 of Example 1 described later), etc. may be used. The concentration of biotin in such a selective solid medium is preferably approximately 0.1 mg/l to 10 mg/l.

The above-described surface color can be confirmed by either comparison with a color sample by visual observation, or measurement using an optical apparatus such as a color-difference meter. When multiple specimens are evaluated, confirmation by visual observation is efficient. The color sample may be, for example, "Determination of Color according to Munsell System, Extended Version" (JAPAN COLOR ENTERPRISE CO., LTD., 2014). The optical apparatus may be, for example, CR-400 (Konica Minolta, Inc.). In addition, if the colony of the *B. subtilis natto* mutant strain is small, it makes difficult to recognize the surface color. Thus, it is preferable to confirm a colony having a diameter of 5 mm or more. Herein, the "diameter" means the maximum diameter among diameters passing the center of an ellipse, when the colony is approximated as an ellipse.

When the surface color is confirmed by comparative observation with a color sample, a dark place is avoided, and it is desirable to measure the surface color under natural lighting or artificial lighting with a moderate illuminance. In order to suppress the influence of lighting or background color, when artificial light is applied from an angle of 45 degrees, it is desirable to confirm from directly above. When artificial light is applied from directly above, it is desirable to confirm from the direction of an angle of 45 degrees.

With regard to the reason why the *B. subtilis natto* mutant strain according to one or more embodiments of the present invention has the above-described surface color, details are unknown. While not wishing to be bound by any particular theory, with regard to the color tone of the surface of a *Bacillus subtilis natto* colony formed on a selective solid medium supplemented with biotin, the region mainly comprising the vegetative cells of *Bacillus subtilis natto* is yellowish milky white, and the region mainly comprising the spores of *Bacillus subtilis natto* is rough white. After a certain period of time has passed after formation of the colony, spores are formed in the center of the colony in the case of ordinary *Bacillus subtilis natto*, and a white region is widely formed. Taking into consideration these facts, it is assumed that, since the *B. subtilis natto* mutant strain according to one or more embodiments of the present invention is a mutant strain having a reduced spore-forming ability under high temperature conditions, a region exhibiting a rough white color is reduced in the colony formed by performing a culture at a high temperature (i.e., a gas phase temperature of 49° C.) due to the factor described in the above requirement.

(c) Carbon Source-Utilizing Properties

The *B. subtilis natto* mutant strain according to one or more embodiments of the present invention has utilizing properties to glucose and sucrose. On the other hand, the present *B. subtilis natto* mutant strain does not have utilizing properties to lactose and arabinose.

(d) Physiological Properties

The *B. subtilis natto* mutant strain according to one or more embodiments of the present invention is an aerobic bacterium, exhibits biotin requirement, and is able to grow in a minimal medium. In addition, the present *B. subtilis natto* mutant strain has protease activity. Moreover, it is able to grow, utilizing citrate.

(e) Temperature Characteristics

The *B. subtilis natto* mutant strain according to one or more embodiments of the present invention has favorable growth capacity at approximately 37° C. to 40° C. that is a temperature zone for the growth of ordinary *Bacillus subtilis natto*. The present *B. subtilis natto* mutant strain proliferates at a proliferation rate that is equivalent to that of ordinary *Bacillus subtilis natto*.

[Spore-Forming Ability]

The spore-forming ability of the *B. subtilis natto* mutant strain according to one or more embodiments of the present invention has temperature sensitivity. The spore-forming ability can be determined using, as an indicator, the measurement results of the number of spores in the culture solution. The number of spores can be measured by subjecting the culture solution to a heat treatment and then obtaining the number of heat-resistant cells using an agar medium.

Specifically, the *B. subtilis natto* mutant strain is inoculated into a liquid medium capable of forming spores (e.g., the medium for spore formation (YE) shown in Table 1 of Example 1 described later), and the medium is then subjected to a shaking culture at a liquid temperature of 37° C. for 24 hours. Thereafter, the obtained solution was heat-treated at 75° C. for 15 minutes, and was then subjected to a smear culture on an LB agar medium (Table 3 of Example 1 described later). After that, the spore-forming ability can be calculated from the number of appearing colonies.

Moreover, the *B. subtilis natto* mutant strain according to one or more embodiments of the present invention has a normal spore-forming ability in a temperature zone that is generally used in a liquid culture for obtaining a *Bacillus subtilis natto* starter. Herein, the "normal spore-forming ability" indicates a spore-forming ability equivalent to that of ordinary *Bacillus subtilis natto*. Specifically, it means the properties of the *B. subtilis natto* mutant strain according to one or more embodiments of the present invention, by which when the colony of the *B. subtilis natto* mutant strain according to one or more embodiments of the present invention is cultured, using a liquid medium for spore formation that is generally used for *Bacillus subtilis natto*, at a liquid temperature of 37° C. the number of spores in the *B. subtilis natto* mutant strain becomes $1\times10^7$ cells/ml or more, preferably $3\times10^7$ cells/ml or more, and more preferably $5\times10^7$ cells/ml or more. Herein, the "medium for spore formation" is not particularly limited, as long as it is a liquid medium comprising medium components such as a carbon source, a nitrogen source, and inorganic salts, wherein the medium enables the formation of the spores of *Bacillus subtilis natto* and the growth thereof, and is commonly used in the culture of *Bacillus subtilis natto*. The medium may be either a synthetic medium or a natural medium. Among such medium components, examples of the carbon source may include: sugars such as glucose, sucrose, galactose, mannose, starch, or a starch decomposed product; and organic acids such as citric acid. Examples of the nitrogen source may include peptone, meat extract, casein hydrolysate, ammonia, ammonium sulfate, and ammonium chloride. Examples of the inorganic salts may include sodium chloride, potassium chloride, calcium chloride, sodium sulfate, sodium hydrogen sulfate, sodium nitrate, potassium phosphate, ferric chloride hexahydrate, magnesium sulfate heptahydrate, manganese chloride tetrahydrate, and ferrous sulfate. In addition, the medium may also comprise yeast extract, malt extract, soybean powder, vitamins (biotin, etc.), and the like. When a *B. subtilis natto* mutant strain requiring specific nutrient components due to gene defect, etc. is used as a parent strain for bleeding, the composition of the medium may be changed, as appropriate. The culture time required for a liquid medium for spore formation at a liquid temperature of 37° C. is not particularly limited. Since the number of spores generally reaches plateau within 48 hours, in general, the culture time is suitably set to be approximately 24 hours to 48 hours.

Moreover, the spore-forming ability of the *B. subtilis natto* mutant strain according to one or more embodiments of the present invention is reduced in a temperature zone generally used in *natto* fermentation. Herein, the phrase "the spore-forming ability is reduced" means the properties of the present *B. subtilis natto* mutant strain whereby when the *B. subtilis natto* mutant strain is inoculated into boiled soybeans or steamed soybeans so that the number of spores of *Bacillus subtilis natto* becomes $5\times10^3$ cells per gram of the boiled soybeans or steamed soybeans, and when the temperature of the soybeans is maintained in the range of 40° C. to 53° C. and fermentation is then continued until favorable stickiness and favorable *natto*-specific flavor can be obtained, the number of spores of *Bacillus subtilis natto* becomes $5\times10^5$ cells or less, preferably $3\times10^5$ cells or less, and more preferably $1\times10^5$ cells or less, per gram of the produced *natto*. Herein, the "*natto*-specific flavor" means a flavor caused by a *natto*-specific flavor ingredient mainly comprising diacetyl, acetoin, pyrazines and the like, which is called "*natto* smell."

[Selection of Strain]

The temperature-sensitive *B. subtilis natto* mutant strain according to one or more embodiments of the present invention can be screened from the natural world. However, it is preferable to use an artificial mutation introduction method because the mutant strain can be efficiently obtained by the method. Examples of such a method of artificially introducing mutation may include chemical methods such as a treatment with a chemical mutagenic agent, physical methods such as ultraviolet ray or X-ray irradiation, and genetic engineering methods. The above-described chemical mutagenic agent is not particularly limited, but examples thereof may include ethyl methanesulfonate (EMS), methyl methanesulfonate (MMS), N-ethyl-N-nitrosourea (ENU), N-methyl-N-nitrosourea (NNU), N-methyl-N'-nitrosoguanidine (NTG), N-methyl-N-nitro-N-nitroguanidine (MNNG), bromodeoxyuridine (BrdU), mitomycin, sodium azide, sodium bisulfite, hydroxylamine, and nucleotide analogues. These mutagenic agents may be used alone as a single type, or may also be used as a mixture of two or more types.

As a parent strain of the *B. subtilis natto* mutant strain, all types of *Bacillus subtilis natto* can be adopted. For example, commercially available common strains, such as Miyagino strain (trade name: Miyagino *Bacillus subtilis natto*) (manufactured by Miyagino Seisakusho), Takahashi strain (trade name: NATTOMOTO) (manufactured by Yuzo Takahashi Laboratory), Naruse strain (trade name: Powdered *Bacillus subtilis natto*) (manufactured by Naruse Hakko Kagaku Kenkusho), and the like can be used. Moreover, various strains, such as mutant strains having specific properties and genetically recombinant strains, can also be used.

It is to be noted that the *Bacillus subtilis natto* No. 7 strain used as a parent strain in the after-mentioned Examples is a strain having a normal spore-forming ability, which was developed by the applicant, and was then deposited as an international deposition with the National Institute of Technology and Evaluation (NITE), Patent Microorganisms Depositary (NPMD) (2-5-8-122, Kazusa Kamatari, Kisarazu-shi, Chiba-ken, Japan, postal code: 292-0818), under Accession No. NITE BP-01805 (identification: *Bacillus subtilis* No. 7) on Feb. 25, 2014.

Specific strains of the *B. subtilis natto* mutant strain according to one or more embodiments of the present invention may include the strains S092, S103, S125, S215, S219, and S238. These strains are obtained by introducing random mutation into the *Bacillus subtilis natto* No. 7 strain according to the method of Example 1 described later, then selecting strains exhibiting a specific surface color when the *B. subtilis natto* mutant strain is cultured at a specific gas phase temperature on a specific selective solid medium, from the above-mutated strains, and then performing multiple stages of selections on the above-selected strains, using, as indicators, spore-forming ability and *natto* fermentation quality under conditions for the production of *Bacillus subtilis natto* starter and *natto*. The thus selected strain is a temperature-sensitive *B. subtilis natto* mutant strain, which has a normal spore-forming ability in a temperature zone that is generally used in a liquid culture for obtaining a *Bacillus subtilis natto* starter, but has a reduced spore-forming ability in a temperature zone that is generally used in *natto* fermentation, and which is used to produce *natto* having excellent quality characteristics.

Among the above-selected strains, a strain comprehensively having the most excellent properties, namely, S103 strain, was deposited as an international deposition with the NITE Patent Microorganisms Depositary (NPMD) (2-5-8-122, Kazusa Kamatari, Kisarazu-shi, Chiba-ken, Japan, postal code: 292-0818), under Accession No. NITE BP-02423 (identification: S103) on Feb. 16, 2017.

As long as the *B. subtilis natto* mutant strain according to one or more embodiments of the present invention retains the spore-forming ability and fermentation quality possessed by the above-selected strains, it also includes *B. subtilis natto* mutant strains derived from the above-selected strains, *B. subtilis natto* mutant strains produced by mutating the above-selected strains, and *B. subtilis natto* mutant strains produced by performing gene introduction into the above-selected strains to transform them. The above-described mutation means a mutation caused by a mutation induction treatment, and such a mutation induction treatment can be carried out using any given suitable mutagen. Examples of the mutagen may include drugs having mutagenic effects and UV irradiation.

Since the *B. subtilis natto* mutant strain according to one or more embodiments of the present invention has a normal spore-forming ability in a temperature zone generally used in a liquid culture for obtaining a *Bacillus subtilis natto* starter, the number of spores of *Bacillus subtilis natto* in the *Bacillus subtilis natto* starter obtained by the liquid culture of the *B. subtilis natto* mutant strain is equivalent to that of ordinary *Bacillus subtilis natto*. Specifically, the number of spores is $1\times10^7$ cells/ml or more, preferably $3\times10^7$ cells/ml or more, and more preferably $5\times10^7$ cells/ml or more.

2. Method for Producing *natto*

In one or more embodiments of the present invention, by producing *natto* using the above-described *B. subtilis natto* mutant strain, it becomes possible to produce *natto* capable of being subjected to heat sterilization.

In one or more embodiments of the present invention, with regard to a method for producing *natto*, *natto* can be produced according to an ordinary method, with the exception that the above-described *B. subtilis natto* mutant strain is used as *Bacillus subtilis natto*.

(1) Immersion and Submerged Heating of Raw Material Soybeans

In the method for producing the *natto* according to one or more embodiments of the present invention, all types of raw materials, which can be used in the production of common *natto*, can be used. Examples of the raw materials that can be used herein may include whole soybeans, half divided soybeans, crushed soybeans (raw materials for split *natto*)), and defatted soybeans. In particular, soybeans having a middle size or a large size, which are used in the production of *natto* having high quality, are preferable. These soybeans can be directly used as raw soybeans, but soybeans subjected to a dry treatment (dry products) are generally used.

In one or more embodiments of the present invention, in order to convert soybeans used as raw materials to steamed soybeans or boiled soybeans according to an ordinary method, the raw material soybeans are subjected to submerged heating. In order to prevent the loss of components, steamed soybeans are preferable. Besides, before performing a steaming or boiling operation, raw material soybeans are preferably immersed in water, so that the soybeans are desirably used in a swollen state.

Herein, as specific procedures for preparing steamed soybeans, a method comprising immersing soybeans in water at normal temperature for approximately 6 to 24 hours, then draining the water away, and then steaming the soybeans with steam at 100° C. to 135° C. for 10 to 30 minutes can be adopted. Moreover, a method of pressurized-steaming soybeans under high-pressure conditions of 0.12 to 0.22 MPa can also be adopted. On the other hand, as specific procedures for preparing boiled soybeans, a method comprising immersing soybeans in water at normal temperature for approximately 6 to 24 hours, and then boiling the soybeans in hot water at 90° C. to 100° C. for 20 to 50 minutes can be adopted.

(2) Inoculation

In the method for producing the *natto* according to one or more embodiments of the present invention, when the above-described *B. subtilis natto* mutant strain is used as a *Bacillus subtilis natto* starter, the mutant strain in the state of spores is preferably used. The *Bacillus subtilis natto* in the state of spores can be stably preserved and can be easily handled. In addition, since it does not die even upon inoculation thereof into hot steamed soybeans or boiled soybeans (hereinafter referred to as "soybeans"), microbial contamination of *natto* can be prevented. Moreover, as a result of heat shock caused by heating, the *Bacillus subtilis natto* in the state of spores can be promptly germinated after it has been inoculated into soybeans.

In order to uniformly perform fermentation, regarding inoculation of the above-described *B. subtilis natto* mutant strain into soybeans, it is desirable to add the mutant strain to the soybeans, so that the soybeans and the *Bacillus subtilis natto* starter become uniform (inoculation, spraying, etc.), and then perform mixing or the like. Preferably, as a *Bacillus subtilis natto* starter, a spore suspension of the *B. subtilis natto* mutant strain is prepared, and it is then added in a liquid state.

Herein, as a spore suspension, a culture solution obtained by culturing the above-described *B. subtilis natto* mutant strain in the aforementioned common liquid medium for spore formation can be used.

The number of *Bacillus subtilis natto* to be inoculated is not particularly limited, as long as it corresponds to a cell concentration according to an ordinary method. It is $1\times10^3$ to $1\times10^6$ cells, preferably $1\times10^3$ to $1\times10^5$ cells, and more preferably $1\times10^3$ to $1\times10^4$ cells, per gram of soybeans.

The temperature of soybeans upon inoculation can be set at 55° C. to 95° C., preferably 60° C. to 95° C., more preferably 65° C. to 95° C., further preferably 70° C. to 90° C., and particularly preferably 75° C. to 90° C. When the temperature of soybeans is lower than the above-described temperature range, microbial contamination is likely to occur. When the temperature of soybeans is higher than the above-described temperature range, the spores of *Bacillus subtilis natto* would die, thereby resulting in poor fermentation.

Soybeans, into which the above-described *B. subtilis natto* mutant strain has been inoculated, are filled into an individual vessel for one or several meals, and thereafter, the soybeans are preferably subjected to the aforementioned fermentation in the individual vessel. In addition, as a traditional method, fermentation can also be carried out by filling the soybeans into a boiled "warazuto" (straw wrapper). Moreover, it is also possible to carry out fermentation in a vessel with a volume of several litters, etc. However, as the value of the volume increases with respect to the surface area, it becomes difficult to transmit a temperature change to the soybeans disposed in the center portion of the vessel. Taking into consideration this fact, it is not desirable to use a large vessel.

Herein, all types of vessels can be used as individual vessels, as long as soybeans can be filled therein. Moreover, when the after-mentioned heat sterilization is carried out, a vessel endurable to the heat treatment is used. Specific examples of the individual vessel that can be used herein may include: vessels molded using expanded sheets made of various types of synthetic resins including styrene-modified polyolefin-based resins, polystyrene-based resins such as polystyrene, high impact polystyrene or a styrene-ethylene copolymer, polyolefin-based resins such as polyethylene, polypropylene or an ethylene-vinyl acetate copolymer, and polyester-based resins such as polyethylene terephthalate; and cup-shaped vessels made of papers, which are commonly used for *natto*. Furthermore, the vessel preferably has a shape, in which *natto* can be directly muddled (stirred) before eating. Further, the vessel preferably has an aspect, in which after completion of the fermentation, the vessel can be sealed with a lid or a sealing.

(3) Fermentation

In the method for producing the *natto* according to one or more embodiments of the present invention, *natto* can be fermented by substantially maintaining the temperature of soybeans in an ordinary *natto* fermentation temperature zone that is 40° C. to 53° C., and preferably 43° C. to 50° C. In addition, in one or more embodiments of the present invention, room temperature is maintained in a temperature zone that is 35° C. to 51° C., and preferably 38° C. to 47° C. so that the temperature of soybeans during fermentation can be maintained in the above-described temperature zone. This is because the temperature of the soybeans is increased by heat of fermentation, so that it is maintained in the above-described temperature zone.

The predetermined time (fermentation time) in which the temperature of soybeans is maintained in the fermentation temperature zone is not particularly limited, but it may be 10 to 24 hours, preferably 12 to 22 hours, and particularly preferably 15 to 20 hours. By progression of the fermentation in the present temperature zone, *natto*-specific flavor/taste, soft texture specific to *natto*, the property of forming long stringy threads (stickiness) may be increasingly given to the *natto*.

Besides, the phrase "substantially maintaining . . . in a *natto* fermentation temperature zone" does not mean that the temperature of soybeans is definitely not deviated from the aforementioned temperature zone, but it means that even in a case where the temperature of soybeans is deviated from the temperature zone, if it is, for example, in a slight temperature range (e.g., within 2° C., preferably within 1° C.) for a slight period of time (e.g., within 10 minutes, preferably within 5 minutes), such a temperature deviated from the temperature zone is considered to satisfy the present fermentation conditions.

(4) Heat Sterilization

Since the spore-forming ability of the aforementioned *B. subtilis natto* mutant strain is reduced in a temperature zone generally used in *natto* fermentation, after completion of the above-described fermentation, a majority of *Bacillus subtilis natto* contained in *natto* is converted to vegetative cells having low heat resistance. As such, *natto* is heart-treated under conditions for killing (significantly reducing) the vegetative cells of *Bacillus subtilis natto*, so that *natto* can be effectively sterilized. Accordingly, in the method for producing the *natto* according to one or more embodiments of the present invention, after completion of the fermentation, a heat sterilization treatment is preferably carried out.

In one or more embodiments of the present invention, the term "after completion of the fermentation" is used to mean both "after the passage of the fermentation" and "in continuation of the termination of the fermentation." Thus, it does not necessarily mean after the fermentation has been completely terminated. In one or more embodiments of the present invention, the "heat sterilization" that can be performed on the *natto* after completion of the fermentation generally means a treatment by which the total number of cells of *Bacillus subtilis natto* contained in the *natto* (approximately $1 \times 10^8$ cells/gram of *natto*) is converted to $1 \times 10^6$ cells/gram of *natto* or less by heating.

The treatment conditions applied in the heat sterilization according to one or more embodiments of the present invention can be determined to be conditions for killing (significantly reducing) the vegetative cells of common *Bacillus subtilis natto* (parent strain). Specific treatment conditions are 55° C. to 100° C., preferably 60° C. to 90° C., more preferably 60° C. to 75° C., and 30 to 200 minutes, preferably 60 to 180 minutes, more preferably 90 to 150 minutes, particularly preferably 110 to 130 minutes. At this time, the humidity can be set to be 0 to 60% at a relative humidity. This heat sterilization may be carried out at multiple stages, while changing the treatment conditions.

(5) Aging

After completion of the above-described heat sterilization treatment, in order to suppress harmful effects caused by secondary fermentation (an increase in ammonia, precipitation of tyrosine, decomposition of threads, etc. caused by activation of *Bacillus subtilis natto* on the *natto* after completion of the fermentation step), in general, aging is carried out at a low temperature of generally 3° C. or higher and lower than 10° C., preferably 3° C. or higher and lower than 8° C., and more preferably 3° C. or higher and lower than 6° C., for 6 hours to 3 days, preferably 8 hours to 2 days, and more preferably approximately 24 hours, and then the production is completed.

3. *Natto*

The *natto* according to one or more embodiments of the present invention produced by the above-described method has the following properties.

(a) Content of Spores

The *natto* according to one or more embodiments of the present invention has a small content of the spores of *Bacillus subtilis natto*, in comparison to common *natto*. This is because the present *B. subtilis natto* mutant strain has a reduced spore-forming ability in a temperature zone generally used in *natto* fermentation, and thus, the spore-forming ability of the *B. subtilis natto* mutant strain is significantly low during the fermentation step. The number of spores of *Bacillus subtilis natto* in common *natto* is approximately $1 \times 10^7$ cells to $1 \times 10^9$ cells per gram of *natto*. However, the number of spores of *Bacillus subtilis natto* in the *natto* according to one or more embodiments of the present invention is $5 \times 10^5$ cells or less, preferably $3 \times 10^5$ cells or less, and more preferably $1 \times 10^5$ cells or less, per gram of *natto* immediately after termination of the fermentation step.

Accordingly, even in a case where the *natto* according to one or more embodiments of the present invention is used as a raw material for processed food products, it is unlikely to be contaminated by spores in the production line of a plant. Therefore, the *natto* according to one or more embodiments of the present invention can be applied to a wide range of processed food products.

The number of spores in the *natto* can be measured, for example, by heat-treating a *natto* suspension, and then obtaining the number of heat-resistant cells using an agar medium. Specifically, *natto* is placed in a bag with a filter included with a paddle-type blender "Stomacher™"

(Seward, UK), and a phosphate buffer is then injected into the bag. Thereafter, the natto suspension suspended with the above-described Stomacher is further diluted with a phosphate buffer, and the obtained solution is then heat-treated at 75° C. for 15 minutes. Thereafter, the reaction solution is subjected to a smear culture on an LB agar medium (Table 3 described later), and the number of spores can be calculated from the number of colonies appearing in the obtained culture.

(b) Total Number of Cells of *Bacillus subtilis natto*

In a case where the heat sterilization step is carried out after completion of the fermentation in the above-described production method, the total number of cells of *Bacillus subtilis natto* in the produced natto according to one or more embodiments of the present invention is smaller than that in common natto that is produced without heat sterilization after completion of the fermentation. Specifically, although it is different depending on heat sterilization treatment conditions, the total number of cells of *Bacillus subtilis natto* immediately after the production of natto can be set to be $1 \times 10^6$ cells or less, preferably $5 \times 10^5$ cells or less, more preferably $3 \times 10^5$ cells or less, further preferably $1 \times 10^5$ cells or less, and particularly preferably $8 \times 10^4$ cells or less, per gram of the natto.

Herein, the total number of cells of *Bacillus subtilis natto* (the sum of spores and vegetative cells) can be measured by obtaining the number of cells in a natto suspension, using an agar medium. Specifically, natto is placed in a Stomacher bag, a phosphate buffer is then injected into the bag, the natto suspension suspended with the above-described Stomacher is further diluted with a phosphate buffer, and the obtained solution is then subjected to a smear culture using an LB agar medium, so that the total number of cells of *Bacillus subtilis natto* can be calculated from the number of colonies appearing in the obtained culture.

(c) Quality of natto

The natto according to one or more embodiments of the present invention produced by the above-described method has a sufficient property of forming long stringy threads (stickiness) and a natto-specific flavor.

4. Method for Reducing Spores and Vegetative Cells of *Bacillus subtilis natto*

In one or more embodiments of the present invention, natto is produced according to the above-described method, so that natto, in which the contents of the spores and vegetative cells of *Bacillus subtilis natto* are reduced, can be produced. Accordingly, one or more embodiments of the present invention provide a method for reducing the spores and vegetative cells of *Bacillus subtilis natto* in natto, which is characterized in that the natto is produced using the above-described *B. subtilis natto* mutant strain.

In one or more embodiments of the present invention, after completion of the natto fermentation, the above-described heat sterilization step is carried out, so that the spores and vegetative cells of *Bacillus subtilis natto* in the natto, in particular, the content of vegetative cells can be significantly reduced. The treatment conditions applied in the heat sterilization are as described above. That is, the treatment conditions can be set to be, for example, 55° C. to 100° C., preferably 60° C. to 90° C., more preferably 60° C. to 75° C., and 30 to 200 minutes, preferably 60 to 180 minutes, more preferably 90 to 150 minutes, particularly preferably 110 to 130 minutes. At this time, the humidity can be set to be 0 to 60% at a relative humidity. As mentioned above, the heat sterilization may be carried out at multiple stages, while changing the treatment conditions.

5. Method for Screening for *Bacillus subtilis natto*

According to one or more embodiments of the present invention, there is also provided a method for screening for *Bacillus subtilis natto* having a reduced spore-forming ability in a natto fermentation temperature zone, using the surface color of the above-described single colony as an indicator. The screening method according to one or more embodiments of the present invention comprises: a step of culturing a test *Bacillus subtilis natto* in a selective solid medium supplemented with biotin at a gas phase temperature of 49° C. for 48 hours; and a step of analyzing the surface color of a single colony of the test *Bacillus subtilis natto* formed on the selective solid medium as a result of the aforementioned culture. Selection is carried out based on whether or not the surface color satisfies the requirement that "when the total area of the surface of the single colony is set at 100%, the area of a region having the hue of yellow (Y), a value of 9 or more and a chroma of 2 or less according to the Munsell Color System is 20% or less." The test *Bacillus subtilis natto* may be any one of strains isolated from the natural world, strains separated from various types of fermented food products, and mutant strains obtained by mutating the aforementioned strains by applying chemical methods such as a chemical mutagenic agent treatment, physical methods such as ultraviolet ray or X-ray irradiation, or genetic engineering methods.

EXAMPLES

One or more embodiments of the present invention will be described in the following Examples. However, these Examples are not intended to limit the scope of the present invention.

(Example 1) Bleeding of *B. subtilis natto* Mutant Strain, and Evaluation of Spore-Forming Ability and natto Production Suitability thereof 1. Preparation of Spore Solution

*Bacillus subtilis* No. 7 strain (NITE BP-01805) was used as a parent strain for breeding a *B. subtilis natto* mutant strain. The No. 7 strain was inoculated in 10 ml of a medium for spore formation (YE)/test tube, as shown in the following Table 1, and the obtained mixture was then subjected to a shaking culture at 37° C. at 150 rpm for 24 hours, to prepare a spore solution.

TABLE 1

| Medium for spore formation (YE) | | |
|---|---|---|
| Yeast extract * | 20.0 | g/l |
| NaCl | 5.0 | g/l |
| pH (Adjusted with NaOH) | 7.1 | |

* Meast™ P2G (manufactured by ASAHI FOOD & HEALTHCARE, LTD.)

2. Chemical Mutation Treatment of Spore Solution

For the chemical mutation treatment of a spore solution of *Bacillus subtilis natto*, mutation cocktail MBS001 (CHITOSE LABORATORY) was used as a mutagenic agent, and the following operations were carried out.

First, 5 µl of a spore solution of the aforementioned No. 7 strain was inoculated into 5 ml of the LB medium shown in the following Table 2, which was filled into a test tube, and the obtained mixture was then subjected to a shaking culture at 37° C. at 150 rpm for 15 hours. Subsequently, LB media supplemented with 4 µg/ml or 8 µg/ml mutation cocktail were added in an amount of 5 ml each into a test tube, and the spore culture solution obtained by the above-described operations was inoculated therein, so that the absorbance at a wavelength of 660 nm became about 0.01. Thereafter, the absorbance was measured over time at 37° C. at 150 rpm, and the reaction mixture was subjected to a shaking culture until the absorbance became about 1.0, thereby obtaining a mutation-treated solution. It is to be noted that the ultraviolet and visible spectrophotometer UV-1800 (Shimadzu Corporation) was used in the above-described measurement of the absorbance.

TABLE 2

| LB medium | | |
|---|---|---|
| Bacto Trypton | 10.0 | g/l |
| Yeast extract | 5.0 | g/l |
| NaCl | 5.0 | g/l |
| pH (Adjusted with NaOH) | 7.0 | |

The total number of cells of the *B. subtilis natto* mutant strain contained in the mutation-treated solution was measured by diluting the mutation-treated solution with a 50 mM sodium phosphate buffer (pH7) to an appropriate concentration, then smearing the diluted solution on the LB agar medium shown in the following Table 3, and culturing it in an incubator in which a gas phase temperature was set at 37° C. for approximately 18 hours, and then calculating the total number of the cells from the number of colonies appearing in the obtained culture. As a result, the total numbers of cells of the *B. subtilis natto* mutant strain of the mutation-treated solution containing 4 μg/ml or 8 μg/ml the mutation cocktail were found to be $5.2 \times 10^8$ cells/ml and $3.3 \times 10^7$ cells/ml, respectively.

TABLE 3

| LB agar medium | | |
|---|---|---|
| Bacto Trypton | 10.0 | g/l |
| Yeast extract | 5.0 | g/l |
| NaCl | 5.0 | g/l |
| Agar | 15.0 | g/l |
| pH (Adjusted with NaOH) | 7.0 | |

3. Screening for Strain having Reduced Spore-Forming Ability in *natto* Fermentation Temperature Zone, Using Surface Color of Single Colony as Indicator Selection of a strain having a reduced spore-forming ability under a high temperature culture from mutation-treated strains was carried out by the following procedures.

First, the mutation-treated solution (containing 4 μg/ml or 8 μg/ml mutation cocktail) was appropriately diluted with a 50 mM sodium phosphate buffer (pH7). The diluted solution was then smeared on each of 150 plates filled with 20 ml of the agar medium for spore formation (containing B) shown in the following Table 4, and it was then cultured in an incubator in which a gas phase temperature was set at 49° C. for 48 hours. Besides, regarding the dilution of the mutation-treated solution, the dilution rate, at which the number of colonies on each plate after the culture became approximately 150, had previously been calculated according to a preliminary experiment. As a result of the culture, approximately 45000 single colonies were obtained.

TABLE 4

| Agar medium for spore formation (containing B) | | |
|---|---|---|
| Bacto nutrient broth (Difco) | 8.0 | g/l |
| KCl | 1.0 | g/l |

TABLE 4-continued

| Agar medium for spore formation (containing B) | | |
|---|---|---|
| $MgSO_4 \cdot 7H_2O$ | 0.12 | g/l |
| Solution 1*[1] | 1.0 | ml/l |
| 100 mg/l biotin | 10.0 | ml/l |
| Agar | 15.0 | g/l |
| pH (Adjusted with NaOH) | 7.0 | |

*[1] Solution 1

| | | |
|---|---|---|
| $CaCl_2$ | 111.0 | g/l |
| $MnCl_2$ | 1.26 | g/l |
| $FeSO_4$ | 0.05 | g/l |

Next, among the above-described single colonies, single colonies having a diameter of 5 mm or more were evaluated in terms of surface color. The evaluation was carried out under an illuminance of about 1500 lux, having, as light sources, natural light coming through a window apart from the experimental stand and fluorescent light irradiated directly above the plate. The plate was placed on a black experimental stand, and upon comparison with a color sample and evaluation, the plate was observed from the direction of an angle of 45 degrees. The surface color of the single colony was evaluated with naked eyes by comparing the single colony with the color sample included with "Determination of Color according to Munsell System, Extended Version" (JAPAN COLOR ENTERPRISE CO., LTD., 2014). The evaluation was carried out based on whether or not the color tone on the surface of the single colony (surface color) satisfies the criteria that "when the total area of the surface of the single colony is set at 100%, the area of a region having the hue of yellow (Y), a value of 9 or more and a chroma of 2 or less according to the Munsell Color System is 20% or less." As a result, 270 *B. subtilis natto* mutant strains satisfying the aforementioned criteria were selected. FIG. 1 is a schematic view of the above-described evaluation. The region having the hue of yellow (Y), a value of 9 or more and a chroma of 2 or less according to the Munsell Color System may be divided into several regions, as shown in FIG. 1, panel (b).

Figure 2:
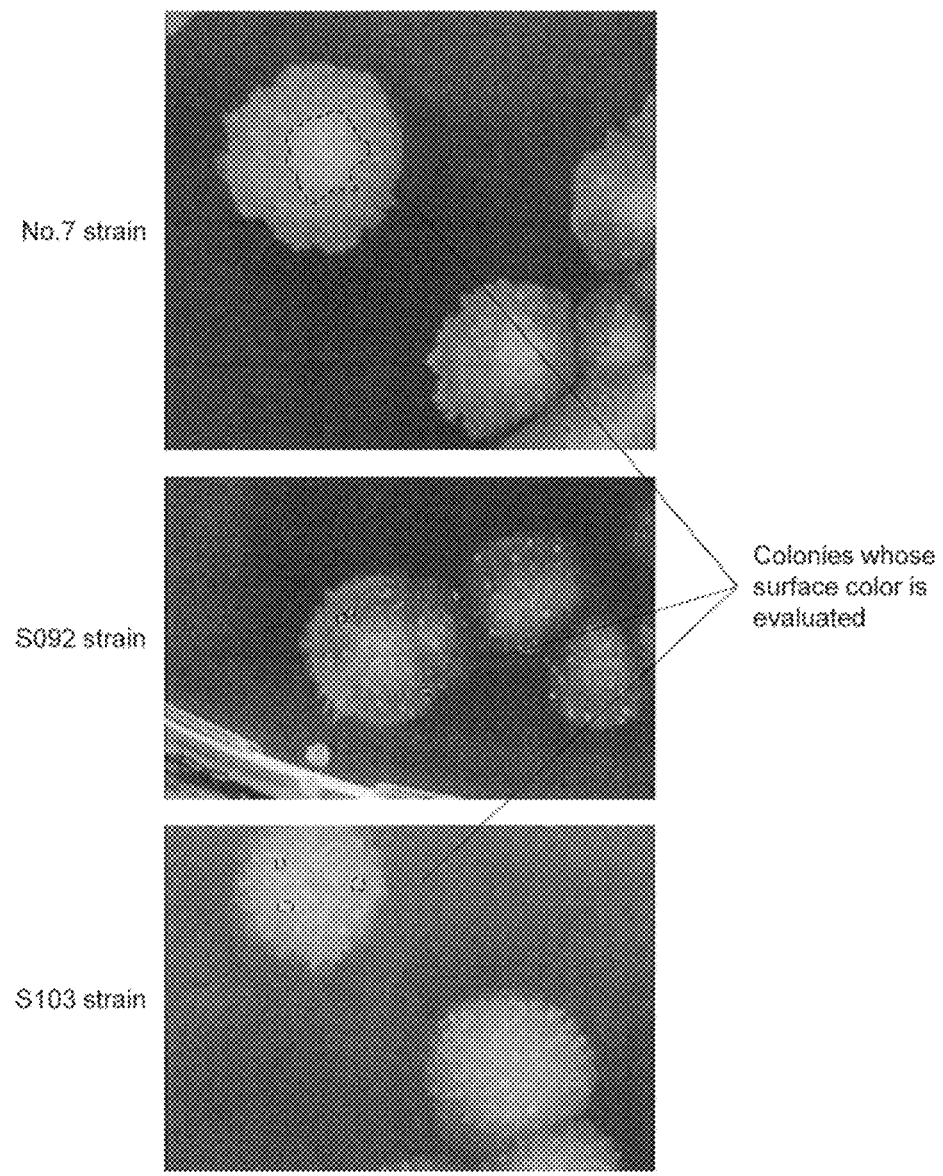
FIG. 2 includes photographs of the colonies of the *B. subtilis natto* mutant strains according to one or more embodiments of the present invention (S092 strain and S103 strain) and a parent strain as a comparative example (No. 7 strain), formed on the selective solid medium (wherein the region surrounded by the dotted line: a region having the hue of yellow (Y), a value of 9 or more and a chroma of 2 or less according to the Munsell Color System).

Among the *B. subtilis natto* mutant strains selected by the above-described evaluation, the colonies of the S092 strain and the S103 strain, and the colonies of the No. 7 strain as a parent strain were photographed. The photographs are shown in FIG. 2. The photographs were taken using a digital camera (finepix f31fd (FIJI FILM)) under fluorescent light. The photographed images exhibited surface colors equivalent to those of the colonies directly observed with naked eyes. In FIG. 2, the region surrounded by the dotted line indicates a region having the hue of yellow (Y), a value of 9 or more and a chroma of 2 or less according to the Munsell Color System. As shown in FIG. 2, the No. 7 strain concentrically had a large, roughly white region having the hue of yellow (Y), a value of 9 or more and a chroma of 2 or less according to the Munsell Color System in the center of the colony, and the area of the region exceeded 20% of the total area of the colony surface. On the other hand, in the S092 strain and the S103 strain, a few regions having the hue of yellow (Y), a value of 9 or more and a chroma of 2 or less according to the Munsell Color System were scattered, but even though the regions were added up, the obtained area was less than 10% of the total area of the colony surface.

Next, in order to eliminate pseudo-positive strains from the above-described 270 candidate strains, a reproduction test was carried out. Specifically, the colonies were streaked on an LB agar medium, and were then cultured at a gas phase temperature of 37° C. for approximately 18 hours. Thereafter, the obtained culture was streaked again on an agar medium for spore formation (containing B), and was then cultured at a gas phase temperature of 49° C. for 48 hours. Thereafter, the formed colonies were subjected to the above-described evaluation again, and only *B. subtilis natto* mutant strains satisfying the aforementioned criteria were selected.

In addition, in order to confirm the polyglutamic acid-producing ability of the candidate strains, the candidate strains cultured on an LB agar medium were streaked on the GSP agar medium shown in the following Table 5, using an inoculating loop, and were then cultured in an incubator at a gas phase temperature of 37° C. for approximately 18 hours. Thereafter, strains, which had formed viscous substances on the cultured colonies art a level equal to or more than the No. 7 strain as a parent strain for bleeding, were determined to be satisfactory.

TABLE 5

| GSP agar medium | | |
|---|---|---|
| Phyton Peptone | 15.0 | g/l |
| Sodium glutamate monohydrate | 15.0 | g/l |
| Glucose | 15.0 | g/l |
| Agar | 15.0 | g/l |

As a result of the above-described colony surface color confirmation tests carried out twice on an agar medium for spore formation (containing B) and viscous substance production test carried out on a GSP agar medium, the candidate strains were narrowed down to 112 strains.

4. Evaluation of *natto* Production Suitability of Candidate Strains (a) Preparation of Spore Solution Next, the colonies of the candidate strains were collected using an inoculating loop, and were then inoculated into 5 ml of a yeast extract medium, followed by performing a shaking culture at 37° C. at 150 rpm for 24 hours, thereby preparing a spore solution for use in the production of *natto* (*Bacillus subtilis natto* spore starter). In addition, the number of spores contained in the obtained spore solution (*Bacillus subtilis natto* spore starter) was measured by diluting the spore solution with a 50 mM sodium phosphate buffer (pH7) to an appropriate concentration, then heating the diluted solution at 75° C. for 15 minutes, then smearing the reaction solution on an LB agar medium, then culturing it in an incubator in which a gas phase temperature was set at 37° C. for approximately 18 hours, and then calculating the number of spores from the number of colonies appearing in the obtained culture.

(b) *Natto* Production Test

A *natto* production test was carried out according to the following method. First, a spore solution of the selected *B. subtilis natto* mutant strain was appropriately diluted, and the diluted solution was then added to soybeans immediately after being steamed according to an ordinary method (steamed at a pressure of 0.16 MPa for 24 minutes), so that the number of spores of *Bacillus subtilis natto* became approximately 5000 cells/1 g of the steamed soybeans, followed by fully blending. Thereafter, the obtained mixture was filled in an amount of 45 g each into individual vessels made of polystyrene.

The filled individual vessels were each subjected to fermentation under conditions of a gas phase temperature of 40° C. for 1 hour, 50.5° C. for 5 hours, and 47.5° C. for 6 hours, so as to produce *natto*. As a comparative example, the No. 7 strain used as a parent strain for bleeding was also treated by the same method as described above to produce *natto*. The fermented *natto* was aged at 4° C. for 24 hours in a refrigerator, and was then evaluated in terms of the quality thereof (the property of forming long stringy threads and a *natto*-specific flavor) according to the following evaluation criteria. With regard to evaluation of the property of forming long stringy threads and a *natto*-specific flavor, a mean value was calculated from the scores of a total of six professional inspectors.

[Evaluation Criteria of Property of Forming Long Stringy Threads]

Figure 3A:
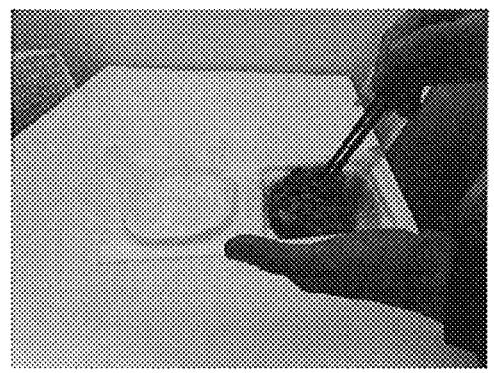
FIGS. 3A to 3C are photographs showing a *natto* stickiness test (A. a state in which *natto* is stirred; B. a state in which the stirred *natto* is lifted up, and C. a state in which the lifted *natto* is dropped).
Figure 3B:
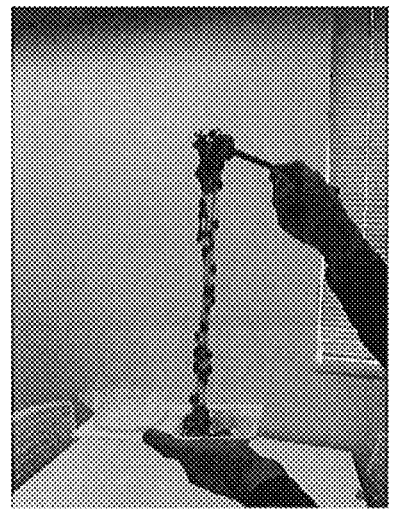
Figure 3C:

As shown in FIGS. 3A to 3C, after *natto* had been stirred with chopsticks 30 times/10 seconds, a mass of *natto* beans was picked up with the chopsticks, and thereafter, the property of forming long stringy threads was evaluated based on the degree at which the *natto* beans were hardly dropped from the chopsticks.

5 points: extremely strong (when a mass of the stirred *natto* beans is picked up with chopsticks, it is retained in the air and is not dropped for 5 seconds or more.)

4 points: strong (when a mass of the stirred *natto* beans is picked up with chopsticks, it is retained in the air for 3 seconds before it is dropped.)

3 points: normal (when a mass of the stirred *natto* beans is picked up with chopsticks, it cannot be retained in the air but the *natto* beans are dropped.)

2 points: weak (stringy threads are formed, but a mass of the stirred *natto* beans is not formed.)

1 point: extremely weak (no stringy threads are formed.)

[Evaluation Criteria of *natto*-Specific Flavor]

The *natto*-specific flavor was evaluated according to sensory evaluation using the following scales.

3 points: the *natto* has a moderate *natto* smell and is favorable without having unpleasant odor.

2 points: the *natto* has a *natto* smell, but unpleasant odor is slightly felt.

1 point: unpleasant odor is strongly felt.

Moreover, the number of spores contained in the *natto* subjected to quality evaluation was measured by the following method. That is, a 50 mM phosphate buffer (pH7) was added to approximately 45 g of *natto*, and the *natto* was then suspended therein using Stomacher (manufactured by ORGANO, EXNIZER 400) at 230 rpm for 1 minute. Thereafter, the suspension was diluted with the same buffer as described above to an appropriate concentration. The diluted extract was heat-treated at 75° C. for 15 minutes, and was then subjected to a smear culture (37° C., 16 hours) on an LB agar medium. After that, the number of spores was obtained from the number of appearing colonies.

With regard to the above-described evaluation items, a *natto* mutant strain satisfying all of the following requirements was determined to be satisfactory: the score of the property of forming long stringy threads is 3 or more points; the score of the *natto*-specific flavor is 3 or more points; the number of spores of *Bacillus subtilis natto* contained in the *natto* is $5 \times 10^5$ cells/gram of *natto* or less; and *Bacillus subtilis natto* contained in the spore solution (*Bacillus subtilis natto* starter) is $1 \times 10^7$ cells/ml or more.

As a result, 6 strains (S092, S103, S125, S215, S219, and S238) were selected as strains, which satisfied all of the above-described requirements, namely, were able to produce *natto* having favorable quality and also having a small number of spores. The evaluation results of spore solutions for use in the production of *natto* (starters) prepared using these selected strains, the number of spores contained in the produced *natto*, the property of forming long stringy threads, and the *natto*-specific flavor, are shown in the following Table 6.

TABLE 6

| Strain | Natto | | | Starter Number of spores (cells/ml) |
|---|---|---|---|---|
| | Stickiness (pt) | Natto-specific flavor (pt) | Number of spores (cells/g natto) | |
| No. 7 | 3.75 | 3 | $7.4 \times 10^8$ | $7.2 \times 10^8$ |
| S092 | 3.75 | 3 | $2.1 \times 10^4$ | $2.9 \times 10^8$ |
| S103 | 4.0 | 3 | $3.4 \times 10^5$ | $7.6 \times 10^7$ |
| S125 | 4.0 | 3 | $7.2 \times 10^4$ | $8.5 \times 10^7$ |
| S215 | 4.0 | 3 | $8.9 \times 10^4$ | $2.9 \times 10^8$ |
| S219 | 4.0 | 3 | $9.7 \times 10^2$ | $2.0 \times 10^7$ |
| S238 | 3.75 | 3 | $1.0 \times 10^4$ | $6.1 \times 10^8$ |

Furthermore, among these strains, the S103 strain that was comprehensively highly evaluated, while also taking into consideration the after-mentioned heating test, was deposited under Accession No. NITE BP-02423.

Further, using the S092 strain and the S103 strain, whether the same results as those of the above-described tests were obtained even in a temperature zone, in which the temperature of *natto* was slightly low, was confirmed. Specifically, a spore solution of the *B. subtilis natto* mutant strain was appropriately diluted, and the diluted solution was then added to steamed soybeans in the same manner as described above, so that the number of spores of *Bacillus subtilis natto* became approximately 5000 cells/1 g of the steamed soybeans. The thus obtained steamed soybeans were filled in an amount of 45 g each into individual vessels. Thereafter, the individual vessels were subjected to fermentation under conditions of a gas phase temperature of 40° C. for 1 hour, or 45° C. for 11 hours, so as to produce *natto*. The quality of the obtained *natto* was evaluated in the same manner as described above (the property of forming long stringy threads and the *natto*-specific flavor). The results are shown in the following Table 7.

TABLE 7

| Strain | Natto | | |
|---|---|---|---|
| | Stickiness (pt) | Natto-specific flavor (pt) | Number of spores (cells/g natto) |
| No. 7 | 3.5 | 3 | $5.3 \times 10^8$ |
| S092 | 3.5 | 3 | $8.7 \times 10^4$ |
| S103 | 3.5 | 3 | $3.1 \times 10^3$ |

As a result, it could be confirmed that all of the mutant strains satisfied the aforementioned selection criteria even under conditions of a gas phase temperature lower than that in the first test.

(Example 2) Heating Test after *natto* Fermentation

Among the *B. subtilis natto* mutant strains selected in Example 1, four strains, namely, the S092 strain, the S103 strain, the S125 strain and the S219 strain were heated at a temperature capable of sterilizing vegetative cells, following fermentation, and then, whether or not the total number of cells could be reduced was confirmed.

First, soybeans were immersed in water at normal temperature overnight, and were then steamed according to an ordinary method (steamed at a pressure of 0.16 MPa for 24 minutes). A spore solution of the above-described *B. subtilis natto* mutant strain was diluted with sterilized water, and the diluted solution was then added to the soybeans immediately after the steaming, so that the number of spores became 5000 cells/1 g of the steamed soybeans, followed by fully blending. Thereafter, the thus obtained steamed soybeans were filled in an amount of 45 g each into individual vessels made of polystyrene.

The filled individual vessels were each subjected to fermentation under conditions of a gas phase temperature of 40° C. for 1 hour, 50.5° C. for 5 hours, and 47.5° C. for 6 hours, and were then heated under conditions of 70° C. for 2 hours. After completion of the heating, the *natto* was quickly transferred into a refrigerator at 4° C., and was then aged therein. Thereafter, the quality of the *natto*, the total number of cells of *Bacillus subtilis natto*, and the number of spores were confirmed.

As a comparative example, the No. 7 strain used as a parent strain for bleeding was also subjected to the heating test by the same method as described above. Regarding some specimens, before heating at 70° C., they were aged at 4° C., and the quality of the *natto* (the property of forming long stringy threads and the *natto*-specific flavor), the total number of cells of *Bacillus subtilis natto*, and the number of spores were measured by the same method as described above at the time point of termination of the fermentation. The results are shown in Table 8 and Table 9.

TABLE 8

| | Natto at termination of fermentation (before heating at 70° C.) | | | |
|---|---|---|---|---|
| Strain | Stickiness (pt) | Natto-specific flavor (pt) | Total number of cells (cells/g natto) | Number of spores (cells/g natto) |
| No. 7 | 3.75 | 3 | $8.3 \times 10^8$ | $3.0 \times 10^8$ |
| S092 | 4 | 3 | $6.3 \times 10^8$ | $8.9 \times 10^3$ |
| S103 | 3.75 | 3 | $4.2 \times 10^8$ | $3.5 \times 10^3$ |
| S125 | 3.75 | 3 | $7.1 \times 10^8$ | $1.0 \times 10^5$ |
| S219 | 3.75 | 3 | $2.7 \times 10^7$ | $1.1 \times 10^5$ |

TABLE 9

| | Natto after heating at 70° C. | | |
|---|---|---|---|
| Strain | Stickiness (pt) | Natto-specific flavor (pt) | Total number of cells (cells/g natto) |
| No. 7 | 3.5 | 3 | $5.9 \times 10^7$ |
| S092 | 3.75 | 3 | $6.4 \times 10^4$ |
| S103 | 3.5 | 3 | $2.2 \times 10^4$ |
| S125 | 3.5 | 3 | $1.2 \times 10^5$ |
| S219 | 3.5 | 3 | $1.2 \times 10^3$ |

As a result, the total number of cells of *Bacillus subtilis natto* at the time point of termination of the fermentation was $1 \times 10^8$ cells order in all of the *B. subtilis natto* mutant strains. However, the total number of cells of *Bacillus subtilis natto* was found to be $1 \times 10^6$ cells/gram of *natto* or less after heating at 70° C. Thus, vegetative cells other than the spores of *Bacillus subtilis natto* could be almost sterilized, and also, the scores of the property of forming long stringy threads and the *natto*-specific flavor satisfied the criteria. Hence, the quality of the produced *natto* was also favorable.

According to one or more embodiments of the present invention, provided is a novel *Bacillus subtilis natto*, which has a normal spore-forming ability in a temperature zone that is generally used in a liquid culture for obtaining a

*Bacillus subtilis natto* starter for inoculation, but has a reduced spore-forming ability in a temperature zone that is generally used in *natto* fermentation. Using the *Bacillus subtilis natto* strain according to one or more embodiments of the present invention, a *Bacillus subtilis natto* starter comprising the spores of *Bacillus subtilis natto* in a high concentration can be produced by the same method as the conventional method, and thus, *natto* having a small number of spores but having the same quality as conventional common *natto* products regarding other points can be produced. In addition, since the *natto* according to one or more embodiments of the present invention can be subjected to sterilization under heating conditions to an extent that they do not damage the quality of the *natto*, the development of various types of processed food products utilizing high-quality *natto* can be promoted. Therefore, one or more embodiments of the present invention can be used in the production of *natto* and processed food products utilizing the *natto*.

All publications, patents and patent applications cited in the present description are incorporated herein by reference in their entirety.

Although the disclosure has been described with respect to only a limited number of embodiments, those skilled in the art, having benefit of this disclosure, will appreciate that various other embodiments may be devised without departing from the scope of the present invention. Accordingly, the scope of the present invention should be limited only by the attached claims.

What is claimed is:

1. A method of producing *natto*, comprising:
    inoculating a mutant strain of *Bacillus subtilis* var. *natto* onto steamed or boiled soybeans, wherein $1\times10^3$ to $1\times10^6$ spores of the mutant strain per gram of the soybeans are inoculated; and
    fermenting the soybeans inoculated with the mutant strain by maintaining a temperature of the soybeans at 40° C. to 53° C.,
    wherein the number of the mutant strain spores after fermenting the soybeans is $5\times10^5$ or less spores per gram of the fermented soybeans, and
    wherein the mutant strain has the following properties:
    a single colony of the mutant strain cultured in a selective solid medium supplemented with biotin at a gas phase temperature of 49° C. for 48 hours has a region having a hue of yellow (Y), a value of 9 or more, and a chroma of 2 or less, as defined by the Munsell Color System, wherein a surface area of the region is 20% or less of the total surface area of the single colony; and
    the number of the mutant strain spores is $1\times10^7$ spores/ml or more after culturing the mutant strain in a liquid medium for spore formation at a liquid temperature of 37° C.

2. The method according to claim 1, further comprising, after fermenting the soybeans, sterilizing the fermented soybeans at a temperature of 55° C. to 100° C. for 30 minutes to 2 hours.

3. The method according to claim 2, wherein the total cell number of the mutant strain after sterilizing the fermented soybeans is $1\times10^6$ cells or less per gram of the fermented soybeans.

4. The method according to claim 1, wherein the mutant strain is inoculated onto the soybeans having a temperature of 55° C. to 95° C.

5. The method according to claim 1, wherein fermenting the soybeans is performed for 10 to 24 hours.

6. The method according to claim 1, wherein the mutant strain is identified as Accession Number NITE BP-02423.

7. *Natto* produced by the method according to claim 1.

8. The *natto* according to claim 7, wherein the number of the mutant strain spores is $5\times10^5$ spores or less per gram of the fermented soybeans.

9. The *natto* according to claim 7, wherein the total cell number of the mutant strain is $1\times10^6$ cells or less per gram of the fermented soybeans.

10. A mutant strain of *Bacillus subtilis* var. *natto* having the following properties:
    a single colony of the mutant strain cultured in a selective solid medium supplemented with biotin at a gas phase temperature of 49° C. for 48 hours has a region having a hue of yellow (Y), a value of 9 or more, and a chroma of 2 or less, as defined by the Munsell Color System, wherein a surface area of the region is 20% or less of the total surface area of the single colony; and
    the number of the mutant strain spores is $1\times10^7$ spores/ml or more after culturing the mutant strain in a liquid medium for spore formation at a liquid temperature of 37° C.

11. The mutant strain according to claim 10, wherein the mutant strain is identified as Accession Number NITE BP-02423.

12. A method of producing *natto*, comprising the following steps (i) to (iii):
    (i) a step of preparing a mutant strain of *Bacillus subtilis* var. *natto* strain having the following properties:
        a single colony of the mutant strain cultured in a selective solid medium supplemented with biotin at a gas phase temperature of 49° C. for 48 hours has a region having a hue of yellow (Y), a value of 9 or more, and a chroma of 2 or less, as defined by the Munsell Color System, wherein a surface area of the region is 20% or less of a total surface area of the single colony;
    (ii) a step of culturing the mutant strain obtained in (i) in a liquid medium for spore formation at a liquid temperature of 37° C. so that a number of mutant strain spores is $1\times10^7$ spores/ml or more; and
    (iii) a step of fermenting soybeans inoculated with the mutant strain by maintaining a temperature of the soybeans at 40° C. to 53° C., wherein the number of the mutant strain spores after fermenting the soybeans is $5\times10^5$ or less spores per gram of the fermented soybeans.

13. A method of producing *natto*, comprising the following steps (i) and (ii):
    (i) a step of preparing a mutant strain of *Bacillus subtilis* var. *natto* strain having the following properties:
        a single colony of the mutant strain cultured in a selective solid medium supplemented with biotin at a gas phase temperature of 49° C. for 48 hours has a region having a hue of yellow (Y), a value of 9 or more, and a chroma of 2 or less, as defined by the Munsell Color System, wherein a surface area of the region is 20% or less of a total surface area of the single colony; and
    (ii) a step of culturing the mutant strain obtained in (i) in a liquid medium for spore formation at a liquid temperature of 37° C. so that a number of the mutant strain spores.

* * * * *